United States Patent [19]

Bose

[11] Patent Number: 5,178,162
[45] Date of Patent: Jan. 12, 1993

[54] SPLASH AND SPILL RESISTANT EXTREMITY IRRIGATION AND DEBRIDEMENT SURGICAL DRAPE

[76] Inventor: William J. Bose, 5400 N. 39th Ave. Apt. Q153, Gainesville, Fla. 32606

[21] Appl. No.: 868,716

[22] Filed: Apr. 14, 1992

[51] Int. Cl.⁵ .................... A61B 19/00; A61B 19/08
[52] U.S. Cl. ................................. 128/849; 128/853; 128/856
[58] Field of Search ................. 128/849–856; 602/2, 63

[56] References Cited

U.S. PATENT DOCUMENTS

| | | | |
|---|---|---|---|
| 3,153,413 | 10/1964 | Gottfried | 602/63 |
| 3,329,144 | 7/1967 | Liman | 602/3 |
| 3,494,356 | 2/1970 | Melges | 128/849 |
| 3,540,441 | 11/1970 | Collins | 128/855 |
| 3,613,676 | 10/1971 | Endres | 128/856 |
| 3,693,618 | 9/1972 | Madden | 128/855 |
| 3,707,964 | 1/1973 | Patience | 128/856 |
| 3,769,971 | 11/1973 | Collins | 128/856 |
| 3,777,749 | 11/1973 | Collins | 128/856 |
| 3,850,172 | 11/1974 | Cazalis | 128/856 |
| 3,934,582 | 1/1976 | Gorrie | 128/856 |
| 3,968,792 | 7/1976 | Small | 128/856 |
| 3,989,040 | 11/1976 | Lofgren | 128/856 |
| 4,119,093 | 10/1978 | Goodman | 128/856 |
| 4,153,054 | 5/1979 | Boone | 128/856 |
| 4,308,864 | 1/1982 | Small | 128/856 |
| 4,345,699 | 8/1982 | Little | 602/3 |
| 4,957,120 | 9/1990 | Grier-Idris | 128/849 |
| 4,966,135 | 10/1990 | Renfrew | 602/3 |
| 5,107,859 | 4/1992 | Alcorn | 128/849 |

Primary Examiner—Michael A. Brown

[57] ABSTRACT

An improved surgical extremity drape (4) which circumferentially envelops the injured limb creating a self enclosed system through which irrigation and debridement is performed. The drape (4) isolates the injured limb from the remainder of the body as well as the surgical team in order to create a fluid splash barrier to prevent the splash or spill of contaminated blood or surgical irrigants. The drape (4) is made in a atubular form of a clear polyethylene fluid impervious, film (5) with a closed distal end (20) and an open proximal end (10). The limb is placed inside of the drape through a fenestrated liquid resistant rubber stretch seal (12) which prevents the leakage of surgical irrigants. A resealable slit (8) is present to allow access to the extremity for wound care or bone fracture fixation prior to or after irrigation and debridement. In addition, perforated hand fenestrations (16) are provided to allow passage of a gloved hand in order to manipulate the limb during irrigation. Perforated irrigation nozzle fenestrations (18) are provided to allow passage of the irrigation nozzle inside of the drape. A drainage plug (6) is provided for drainage of blood and contaminated irrigation fluids.

10 Claims, 3 Drawing Sheets

SPLASH AND SPILL RESISTANT EXTREMITY IRRIGATION AND DEBRIDEMENT SURGICAL DRAPE

BACKGROUND

1. Field of Invention

This invention relates generally to surgical drapes, more particularly to a surgical drape which isolates the limb upon which surgery is to be performed from the rest of the body, and specifically to such drapes which are adapted to circumferentially envelop a patient's extremity during the operative procedure.

2. Description of Prior Art

Surgeons commonly use the technique of irrigation and debridement on contaminated, or dirty traumatic wounds or on bone fractures which penetrate the skin, prior to closure of such wounds. Irrigation is a thorough cleansing of a wound with a saline solution or other sterile irrigants. Debridement is the removal of foreign matter such as dirt or grass, or removal of dead and devitalized tissue from the wound. The purpose of wound irrigation and debridement is to remove foreign matter or dead tissue from the wound and to decrease the amount of bacteria in a wound prior to closure. This in turn decreases the chance of infection in the wound.

Historically, when surgery is to be performed on a patient's extremity, it has been standard procedure to drape the entire patient with folded linen sheets, yet leave the extremity that is to be operated on accessible and free, so that it can be manipulated in the desired position. This is accomplished by allowing one nurse to elevate the limb while the surgeon and an assistant position drapes under and over the extremity, thereby covering the torso. In this way the prepared surgical limb was said to be "draped free" from the rest of the body, so as to isolate the prepared surgical limb from the rest of the body. Recently, fenestrated surgical drapes are used to isolate the surgical limb. The prepared limb is passed through the fenestration in the drape, and in this manner, the surgical limb is exposed for surgery while isolating it from the remainder of the body.

Once the surgical limb has been draped free, a collection pan is then placed under the wound on the limb, in order to collect the sterile irrigation fluids used during irrigation and debridement. Irrigation and debridement of the wound is then performed using pressurized irrigation solution, either from a hand syringe or from tubing with a nozzle tip. During irrigation, a significant amount of the solution will splash from the limb onto the surgeon, nurse and assistants. Also the pan placed under the limb will not catch all of the irrigation solution, and some of the solution will spill onto the floor as well as the surgeon's and nurse's feet. The splashed or spilled irrigation fluid becomes contaminated by the patient's blood during irrigation. If the patient has a blood borne viral disease such as AIDS, Hepatitis A, B, or C, or Cytomegalovirus, then the surgeon, nurse, or assistants may be at risk for contracture of these diseases through the splash or spillage of the contaminated irrigation fluid.

The prior art has been directed to covering limbs (such as legs) to isolate a surgical area other than the limb, from the limb itself in order to prevent contamination from the unprepared body to the prepared surgical extremity. This has been accomplished recently by the use of nonwoven liquid repellent disposable drapes. Some of these drapes have fenestrations through which the prepared limb is placed in order to isolate said limb from the rest of the body. Examples of patient extremity drapes of this type may be found in U.S. Pat. No. 4,957,120 to Grier-Idris (1990), and 4,119,093 to Goodman (1978). These fenestrated drapes provide a barrier only between the prepared limb and the rest of the body. They do not provide any splash of spill barrier to the surgeon or assistants.

Tubular extremity drapes made of an innerstockinette material and outer liquid proof film are also used to isolate the surgical limb from the rest of the body. Examples of this type may be found in U.S. Pat. Nos. 3,540,441 to Collins (1970), 3,707,964 to Patience and Collins (1973), 3,769,971 to Collins (1973), 3,777,749 to Collins (1973), 3,934,582 to Gornie (1976), 3,968,792 to Small (1976), 3,989,040 to Lofgren and Farrow (1976), and 4,308,864 to Small et al (1982). These tubular extremity drapes, once in place must be then cut open to gain access to the limb prior to irrigation and debridement. Once cut open, the drape is not resealable, the irrigation solution can splash, and a collection pan must be used to collect the irrigation solution. Also, these tubular extremity drapes do not create a fluid resistant seal at the open end.

For gynecological or obstetrical procedures, prior art devices have included a drape having seperate leggings or seperate leg drapes. In all of these patents, the object or area of surgery is other than the extremity which is draped. Examples of these drapes may be found in U.S. Pat. Nos. 3,494,356 to Melges (1970), 3,613,676 to Endres (1971), and 3,693,618 to Madden (1972).

While the previously mentioned inventions are effective in creating a liquid imprevious barrier between the prepared surgical extremity and the rest of the body, they suffer from major distinct disadvantages:

(a) None of these surgical drapes provide a barrier to the surgeon or assistants to splash of contaminated irrigation fluids.

(b) None of these surgical drapes provides a fully enclosed liquid resistant system to collect and drain contaminated irrigant fluids.

(c) None of these surgical drapes provide a slit to provide access to the limb, which is resealable to recreate a fluid splash barrier for further irrigation.

OBJECTS AND ADVANTAGES

Accordingly, besides the objects and advantages of providing a disposable surgical drape that circumferentially covers a patient's limb or extremity during surgery, several other objects and advantages of the present invention are:

(a) to provide a surgical drape which isolates the prepared limb from the unprepared torso or other limbs in order to reduce contamination and infection;

(b) to provide a surgical drape that creates a self enclosed system around the injured limb through which irrigation and debridement is performed, which prevents the splash and spillage of irrigation fluids, blood or bodily fluids;

(c) to provide a surgical drape which creates a liquid resistant seal at the open proximal end of the drape and has a drainage plug at the closed distal end in order to create a closed system around the limb to collect and drain contaiminated irrigants;

(d) to provide a surgical drape which is constructed of a clear flexible fluid impervious plastic surgical wrap for resistance to liquid strike through;

(e) to provide a surgical drape which is constructed of clear plastic surgical wrap which is see-through for easy inspection of the limb by the surgeon;

(f) to provide a surgical drape which is both flexible and does not closely conform to the extremity;

(g) to provide a surgical drape which has a resealable slit to allow access to the extremity for wound care or bone fracture fixation. Once wound care is completed, the slit is resealed and irrigation can be continued.

(h) to provide a surgical drape with perforated fenestrations through which the surgeon may pass a gloved hand in order to manipulate the limb or hold the irrigation nozzle; and (i) to provide a surgical drape with perforated fenestrations through which the nozzle of a pressurized irrigation fluids are passed.

Further objects and advantages of my invention will become apparent from a consideration of the drawings and ensuing description of it.

BRIEF DESCRIPTION OF THE DRAWINGS

The present invention may be better understood by reading the following detailed description of the preferred embodiment with reference to the accompanying drawings wherein.

Figure 1:
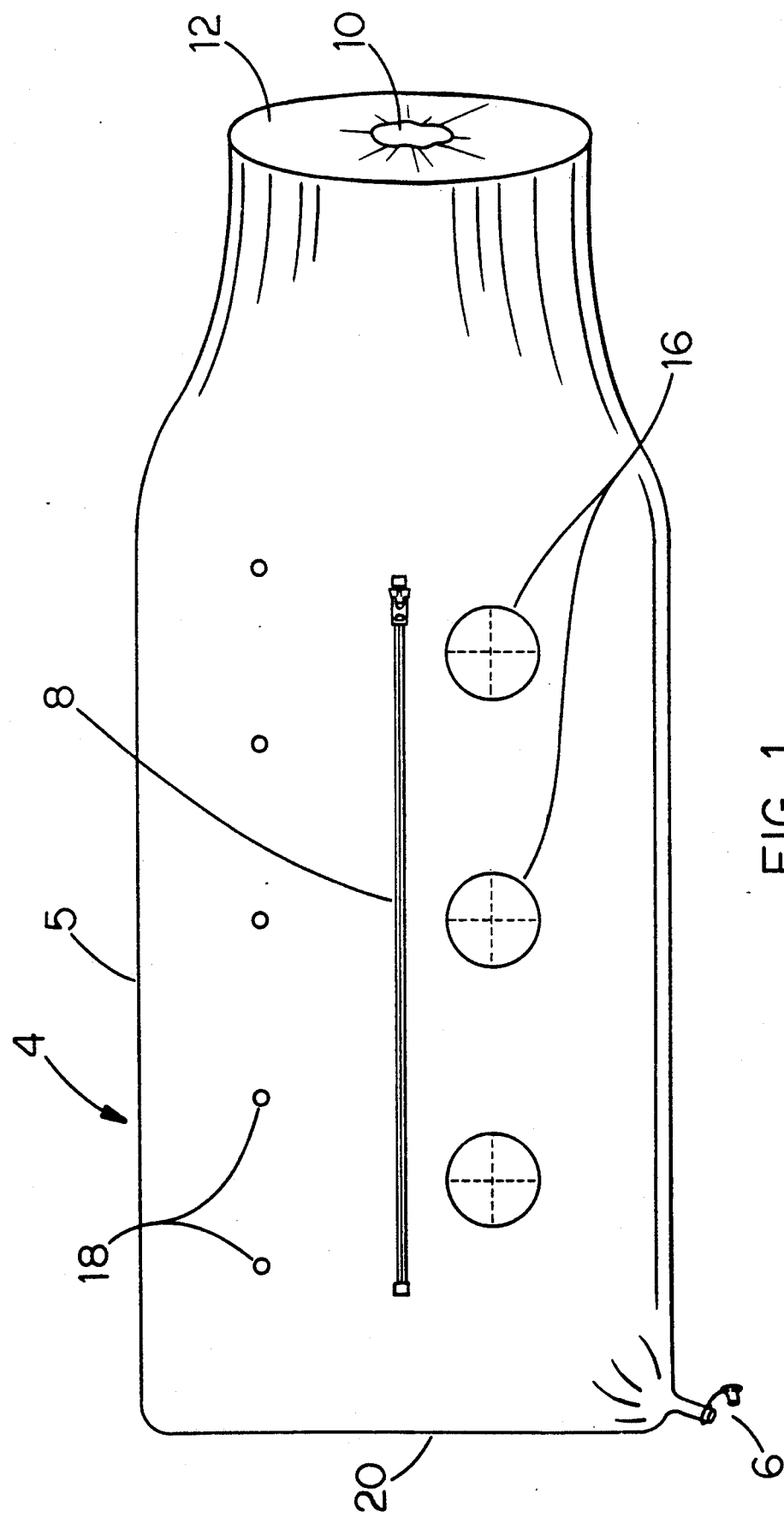
FIG. 1 shows a plain view of a surgical drape according to the present invention.

REFERENCE NUMERALS IN DRAWINGS 4 splash and spill resistant extremity irrigation and debridement surgical drape
5 clear polyethylene fluid impervious film
6 drainage plug
8 resealable plastic slit
10 open proximal end
12 fenestrated liquid resistant rubber stretch seal
16 perforated hand fenestrations
18 perforated irrigation nozzle fenestrations
20 closed distal end

DESCRIPTION OF THE PREFERRED EMBODIMENT—FIGS. 1 AND 2

While the invention will be described in connection with preferred embodiments, it will be understood that it is not intended to limit the invention to those embodiments. On the contrary, it is intended to cover all alternatives, modifications and equivalents as may be included within the spirit and scope of the invention as defined by the appended claims.

Figure 2:
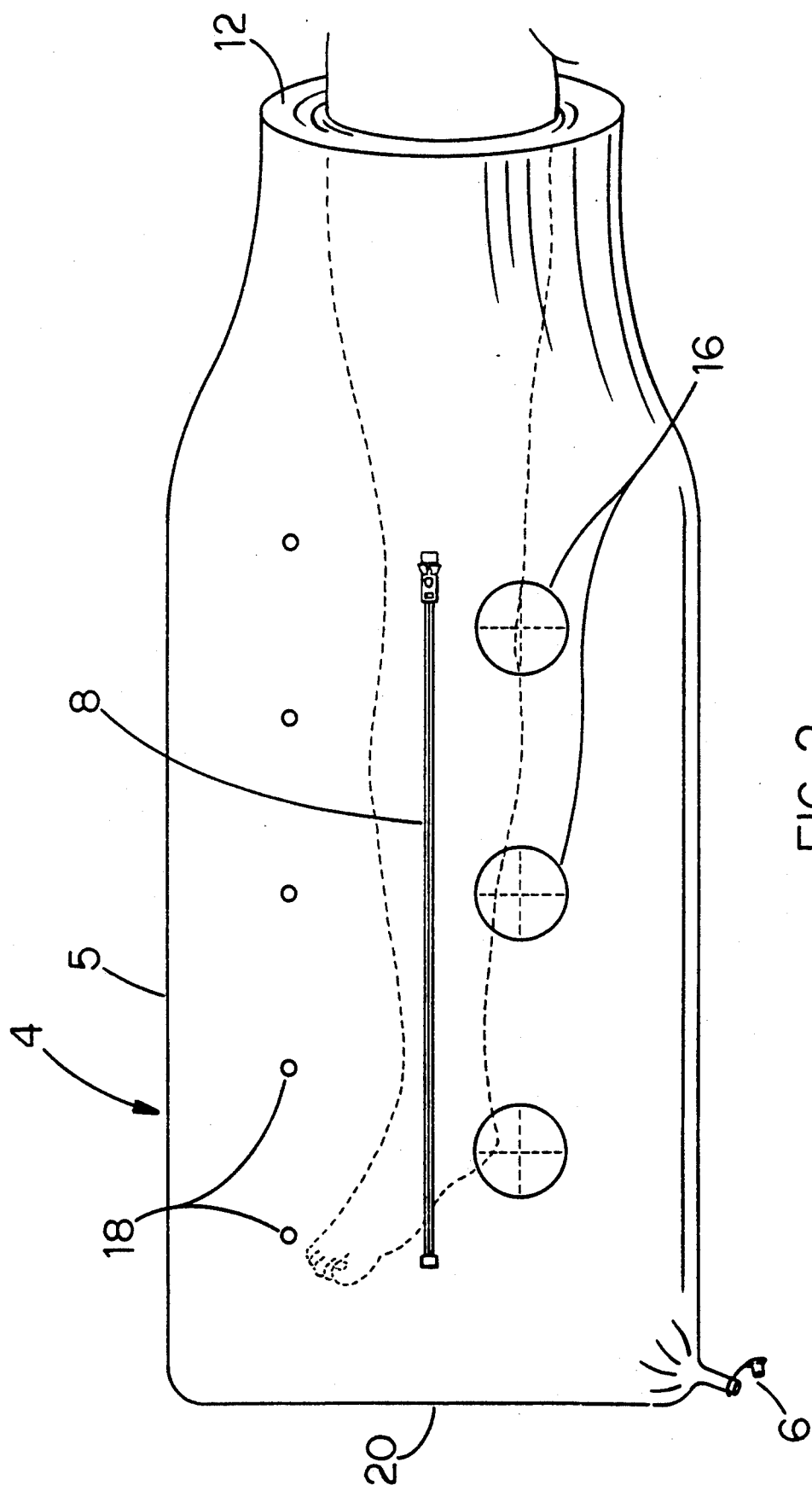
FIG. 2 shows a side elevation illustration of a surgical drape according to the present invention applied to a patient's lower extremity.

With reference now to FIGS. 1 and 2, there is illustrated a splash and spill resistrant extremity irrigation and debridement surgical drape according to the present invention shown generally at 4. In the preferred embodiment, of drape 4, a clear polyethylene fluid impervious film 5 is used, although other vinyl or rubber materials are known to be suitable for resistance to liquid strike through. Drape 4 is shaped generally in a seamless tubular or conical form with a closed distal end 20 and an open proximal end 10. In the preferred embodiment, intended use on a leg, the present invention shown generally at 4 has a flat length of about 110 cm and a width of 46 cm. The circumference of open end 10 is about 90 cm.

Bonded to open proximal end 10 of drape 4 is a fenestrated liquid resistant rubber stretch seal 12. Rubber stretch seal 12 is bonded at its outer circumferential edge to the outer circumferential edge of open proximal end 10 of drape 4. Rubber stretch seal 12 is made of an elastic rubber of vinyl material formed in a circular fashion which has a small fenestration in the center.

A resealable plastic slit 8 is present in the middle of one side of drape 4, and is positioned to extend from the distal portion to the proximal portion of drape 4 (FIG. 2). Slit 8 is a longitudinal plastic zipper which extends for approximately 60 cm in the mid longitudinal axis of drape 4. Multiple perforated hand fenestrations 16 and perforated irrigation nozzle fenestrations 18 are provided in longitudinal arrangement within the drape. Perforated hand fenestrations 16 are about 5 cm in diameter. Perforated irrigation nozzle fenestrations 18 are about 1 cm in diameter.

Drainage plug 6 is provided at closed distal end 20 of drape 4. It is provided with a plastic cap. Irrigation solution and blood that is collected in the bottom of drape 4 is drained via plug 6.

From the description above, a number of advantages of my splash and spill resistant extremity irrigation and debridement surgical drape become evident:

(a) During surgical irrigation, irrigants routinely splash and spill onto the surgeon and surgical team. A surgical drape that envelops the extremity creating a barrier between the surgical team and the extremity will eliminate the splash of irrigants and bodily fluids.

(b) The surgical drape envelops the extremity, and therefore is able to collect and drain contaminated irrigant and bodily fluids, eliminating spillage of these fluids onto the surgical team.

(c) The surgical drape is provided with a resealable slit, which when opened, allows access to the injured limb. The slit can be resealed to allow continued irrigation once the wound has been debrided.

(d) The surgical drape is constructed of clear plastic which allows direct inspection of the extremity during irrigation.

(e) The surgical drape is provided with perforated fenestrations to allow passage of a gloved hand and a irrigation nozzle inside of the drape.

OPERATION—FIG. 3

Figure 3:
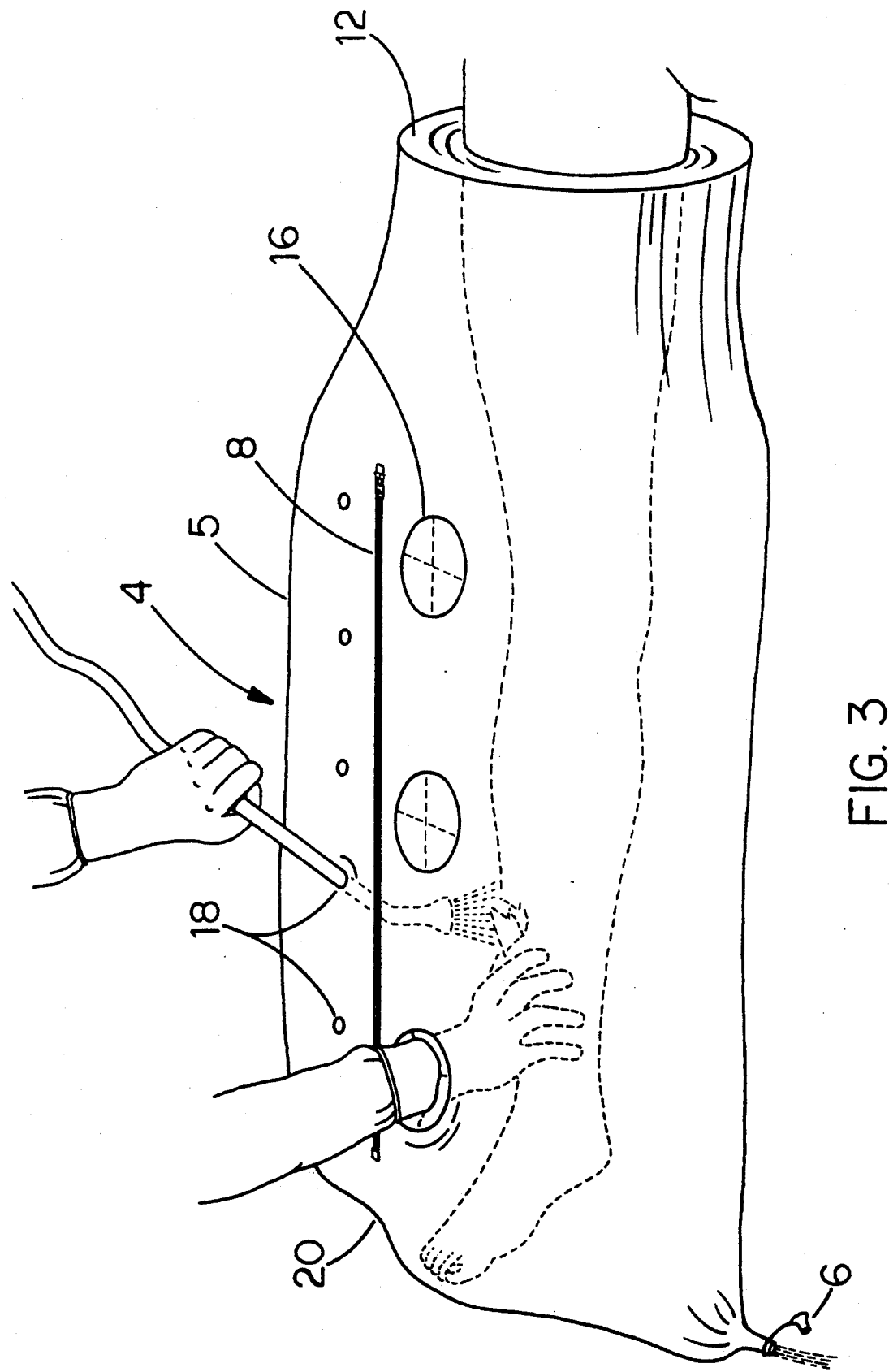
FIG. 3 shows a side elevation illustration of a surgical drape according to the present invention being applied to a patient with a bone fracture and skin laceration undergoing surgical irrigation and debridement.

With reference now to FIG. 3, there is illustrated of the application of drape 4 to the patient's leg. In particular, application is accomplished by placing the patient's foot inside of drape 4 through the fenestration of rubber stretch seal 12 at open proximal end 10 of drape 4. The surgeon then can slip drape 4 over the leg by manually stretching rubber stretch seal 12. The drape may be telescope folded in order to allow it to be unfolded quickly and placed around the patient's appendage. Rubber stretch seal 12 is pulled proximally on the extremity around the leg, and released. When released, the elastic material in rubber stretch seal 12 forms a tight band around the proximal extremity, creating a substantially liquid resistant seal around the extremity. In this manner, an enveloping sterile surgical drape has been placed around the extrimity which isolates the limb from the rest of the body as well as the surgical team. A closed system has been created around the patients limb which will prevent splash or spill of irrigants.

The surgeon then places the nozzle of the pressurized lavage through a chosen perforated irrigation nozzle fenestration 18 by tearing the perforation. His other hand is then placed through a selected perforated hand fenestration 16 by tearing the perforation. Perforated hand fenestrations 16 and perforated irrigation nozzle fenestrations are just large enough to pass a hand or irrigation nozzle through and still create a liquid resistant seal. Pressurized irrigation of the wound is begun. The clear polyethelene fluid impervious film 5 prevents splash of irrigants, blood or other bodily fluids onto the surgeon or surgical team while allowing visual access to the limb and wound during irrigation. In this manner, the surgeon can irrigate the wound with pressurized lavage while manipulating the limb, without being splashed in the face with irrigation solution, blood or other bodily fluids. The irrigation fluid then collects at closed distal end 20, on the inside of drape 4, and is drained through drainage plug 6 via standard surgical tubing.

Once the irrigation is stopped, resealable plastic slit 8 can be opened at any time during the procedure to allow access to the limb for debridement, suture, or bone fracture fixation. Resealable plastic slit 8 can then be closed and subsequent irrigation may procede if necessary. Once the surgical procedure is completed and a dressing placed on the wound, the drape is removed from the leg.

SUMMARY, RAMIFICATIONS AND SCOPE

Thus the reader will see that the surgical drape of the invention provides a transparent, fluid impervious, circumferentially enveloping surgical extremity drape which allows pressure lavage of the extremity while eliminating splash of irrigation fluid, blood or other bodily fluids. It also allows for collection and drainage of these fluids without spillage. Also provided is a resealable slit that allows access to the limb through which a surgical procedure can be done. Once the procedure is completed, the slit is closed and further irrigation can be performed.

While my above descriptions contain many specificities, these should not be construed as limitations on the scope of the invention, but rather as an exemplification of one preferred embodiment thereof. Many other variations are possible. For example, drape 4 can have other shapes such as a circular or rectangular. Resealable slit and perforated hand fenestrations 16 and perforated irrigation nozzle fenestrations 18 can be arranged in alternative places. Resealable slit 8 may be a plastic zipper or a ziplock type seal. Also, drape 4 may be manufactured in various proportional sizes in order to fit larger or smaller patients or upper or lower extremities. Furthermore, other mechanisms to create a liquid resistant seal around the proximal part of the extremity may be employed, such as adhesive strips on the inner circumference of open proximal end 10 of drape 4, or a velcro belt on open proximal end 10 of drape 4. Finally, another variation of my invention is that drape 4 may be made part of or connected to a fenestrated extremity surgical drape, such as those which are presently commercially available.

Accordingly the scope of the invention should be determined not by the embodiment illustrated, but by the appended claims and their legal equivalents.

I claim:

1. A surgical drape for use in limb surgery and isolating an extremity upon which surgery is to be performed, said drape comprising a tube having an open end and a closed end adapted to enclose a patients extremity during surgery on said extremity, wherein said drape comprises:

a slit extending from said closed end partially along the length of said drape and a closure means for reclosure of said slit, an attachment means at said open end of said drape for forming a fluid resistant seal around said extremity, said attachment means is a fenestrated liquid resistant rubber stretch seal at said open end of said drape, a drainage means for drainage of contamination irrigated fluids that collect inside of the drape, perforated hand fenestations, and perforated irrigation nozzle fenestrations in the wall of said drape.

2. The surgical drape according to claim 1 wherein said drape is made of a layer of strong, flexible, liquid impervious film.

3. The liquid impervious film of claim 2 wherein said liquid impervious film is transparent.

4. The fenestrated rubber stretch seal of claim 1 is a circular sheet of stretchable rubber with a hole in the center.

5. The circular sheet of stretchable rubber of claim 4 is mounted at its outer edge to the open circumferential edge of said drape.

6. The surgical drape of claim 1, wherein said closure means is a plastic zipper.

7. The drainage means of claim 1 is a drainage plug.

8. The perforated fenestrations of claim 1 wherein said perforated fenestrations may be torn, to allow the passage of a gloved hand or surgical instruments inside of said drape.

9. The surgical drape of claim 1 wherein said drape is of sufficient length and width to completely enclose said patient's extremity.

10. The surgical drape of claim 1 wherein said drape is flexible and does not closely conform to the extremity.

* * * * *